(12) United States Patent
Sotome et al.

(10) Patent No.: US 7,494,664 B2
(45) Date of Patent: Feb. 24, 2009

(54) COMPOSITE BIOMATERIALS

(75) Inventors: Shinichi Sotome, Tokyo (JP); Toshimasa Uemura, Ibaraki (JP); Junzo Tanaka, Ibaraki (JP); Masanori Kikuchi, Ibaraki (JP); Kenichi Shinomiya, Tokyo (JP); Tetsuya Tateishi, Ibaraki (JP)

(73) Assignees: Japan Science and Technology Agency, Kawaguchi-shi (JP); National Institute of Advanced Industrial Science and Technology, Tokyo (JP); National Institute for Materials Science, Tsukuba-shi (JP)

( * ) Notice: Subject to any disclaimer, the term of this patent is extended or adjusted under 35 U.S.C. 154(b) by 0 days.

(21) Appl. No.: 10/493,388

(22) PCT Filed: Sep. 27, 2002

(86) PCT No.: PCT/JP02/10036

§ 371 (c)(1),
(2), (4) Date: Jan. 7, 2005

(87) PCT Pub. No.: WO03/035128

PCT Pub. Date: May 1, 2003

(65) Prior Publication Data

US 2006/0172918 A1    Aug. 3, 2006

(30) Foreign Application Priority Data

Oct. 25, 2001 (JP) ............................ 2001-328167

(51) Int. Cl.
*A61F 2/02* (2006.01)
*A61F 2/28* (2006.01)
*A61K 38/17* (2006.01)
*C01B 25/32* (2006.01)

(52) U.S. Cl. ................. 424/423; 530/356; 423/308; 623/16.11

(58) Field of Classification Search ................. 424/423; 530/356; 423/308; 623/16.11
See application file for complete search history.

(56) References Cited

U.S. PATENT DOCUMENTS

| | | | | |
|---|---|---|---|---|
| 5,869,080 | A * | 2/1999 | McGregor et al. | 424/426 |
| 5,990,381 | A * | 11/1999 | Nishihara | 424/422 |
| 6,162,258 | A * | 12/2000 | Scarborough et al. | 623/23.63 |
| 6,264,701 | B1 * | 7/2001 | Brekke | 623/23.72 |
| 6,425,918 | B1 * | 7/2002 | Shapiro et al. | 623/11.11 |

FOREIGN PATENT DOCUMENTS

| | | |
|---|---|---|
| JP | 1-207072 | 8/1989 |
| JP | 1-299563 | 12/1989 |
| JP | 11-199209 | 7/1999 |
| WO | WO 98/40111 | 9/1998 |
| WO | WO 9840111 A1 * | 9/1998 |
| WO | WO 0044401 A1 * | 8/2000 |

OTHER PUBLICATIONS

Kikuchi et al., "The biomimetic synthesis and biocompatibility of self-organized hydroxyapatite/collagen composites" Bioceramics 12:393-396, 1999.*
M. Kikuchi et al.; Materials Research Society, Symposium Proceedings, vol. 599, pp. 51-53, 2000. Cited in the PCT search report.
M. Kikuchi et al.; Bioceramics, vol. 12, pp. 393-396, 1999. Cited in the PCT search report.
H. Thiele et al.; J. Biomed. Mater. Res., vol. 3, pp. 431-441, 1969. Cited in the PCT search report.
S. Sotome et al.; The 20th Japanese Society for Transplantation and Tissue Engineering in Musculoskeletal System, 2001.

* cited by examiner

*Primary Examiner*—Jon P Weber
*Assistant Examiner*—Rosanne Kosson
(74) *Attorney, Agent, or Firm*—Westerman, Hattori, Daniels & Adrian, LLP.

(57) ABSTRACT

This invention provides novel composite biomaterials having excellent bioadaptability and bone inductivity and a process for producing the same. The composite biomaterials comprise hydroxyapatite, collagen, and alginate and have microporous structures in which the c-axis of the hydroxyapatite is oriented along the collagen fibers.

14 Claims, 5 Drawing Sheets
(5 of 5 Drawing Sheet(s) Filed in Color)

HAp/Col/alginate complex

Second week

Second week (enlarged view)

Fourth week

Fourth week (enlarged view)

Eighth week

Eighth week (enlarged view)

Commercialized porous hydroxyapatite

Second week

Second week (enlarged view)

Fourth week

Fourth week (enlarged view)

Eighth week

Eighth week (enlarged view)

HAp/Col composite (block)

Second week

Second week (enlarged view)

Fourth week

Fourth week (enlarged view)

Eighth week

Eighth week (enlarged view)

Alginate

Second week

Second week (enlarged view)

Fourth week

Fourth week (enlarged view)

Eighth week

Eighth week (enlarged view)

COMPOSITE BIOMATERIALS

TECHNICAL FIELD

The present invention relates to composite biomaterials comprising hydroxyapatite, collagen, and alginate and a process for producing the same. Particularly, the present invention relates to novel composite biomaterials having mechanical properties similar to those of natural bones, excellent bioadaptability, and excellent bone-conductivity and a process for producing the same.

BACKGROUND ART

In the field of regenerative medicine, a variety of artificial biomaterials that can be used as substituents to damaged tissues or organs have been recently developed. Implants such as artificial bones or artificial bone fillers are used particularly for treatment of bone defects. Such implants, however, are required to have bioadaptability and bone inductivity in addition to mechanical properties similar to those of natural bones. That is, implants needs to be gradually resorbed after implantation in the body, involved into the bone regeneration cycle, and then substituted for the bones of the subject.

Bones of vertebrates are composed of hydroxyapatite and collagen. They forms a specific nanocomposite structure in natural bones characterized in that the c-axis of hydroxyapatite is oriented along the collagen fibers, and this structure imparts bone-specific mechanical properties. Composite biomaterials of hydroxyapatite and collagen having structures and compositions similar to those of natural bones are described in, for example, JP Patent Publication (Kokai) Nos. 7-101708 A (1995) and 11-199209 A (1999), and bone inductivity thereof has been observed to some extent.

Alginic acid is a polysaccharide contained in seaweed, which has been heretofore employed in a haemostatic drug or wound dressing. Concerning artificial bones, development of bone fillers comprising α-TCP in combination with alginate has been reported (Nagata, Shika Zairyou (Dental materials), vol. 16, No. 6, 1997, pp. 479-491). Moreover, alginic acid has been recently reported to help a repair of bones and/or cartilages (e.g., Fragonas et al., Biomaterials 21, 2000, pp. 795-801). Application of alginic acid to a composite of hydroxyapatite and collagen, however, had not yet been attempted. In particular, homogenous incorporation of alginic acid into the composite while maintaining its specific nanocomposite structure involves some difficulties.

DISCLOSURE OF THE INVENTION

An object of the present invention is to provide novel composite biomaterials having excellent bioadaptability and bone inductivity in which alginate is homogenously distributed in a composite of hydroxyapatite and collagen having microporous structures similar to those of natural bones and a process for producing the same.

The present inventors have conducted concentrated studies in order to attain the above object. As a result, they have succeeded in obtaining a composite in which alginate has been homogenously incorporated by adding alginate to a microporous composite of hydroxyapatite and collagen in a given step and curing the mixture. They have found that this composite had excellent bioadaptability and bone inductivity. This has led to the completion of the present invention.

More specifically, the present invention provides the following (1) to (10).

(1) Composite biomaterials, which comprise hydroxyapatite, collagen, and alginate and have a microporous structure in which the c-axis of hydroxyapatite is oriented along the collagen fibers.

(2) The composite biomaterials according to (1), wherein an alginate content is 1 to 30% by mass, relative to the total amount of hydroxyapatite and collagen.

(3) The composite biomaterials according to (2), wherein an alginate content is 5 to 20% by mass, relative to the total amount of hydroxyapatite and collagen.

(4) The composite biomaterials according to any one of (1) to (3), wherein the ratio of hydroxyapatite with collagen is between 60:40 and 90:10.

(5) The composite biomaterials according to (4), wherein the ratio of hydroxyapatite with collagen is between 70:30 and 85:15.

(6) The composite biomaterials according to any one of (1) to (5), in which the alginate is homogenously distributed therein.

(7) The composite biomaterials according to (6), wherein the composite biomaterials after lyophilization have the porosity of 80% or higher.

(8) The composite biomaterials according to (7), which is produced by the following steps:
  1) mixing a composite of hydroxyapatite and collagen with alginate; and
  2) mixing a calcium carbonate suspension with the resulting mixture, mixing gluconic acid powders thereto to cure the mixture, and allowing carbon dioxide to foam, thereby obtaining composite biomaterials.

(9) A process for producing composite biomaterials comprising the following steps:
  1) mixing a composite of hydroxyapatite and collagen with alginate; and
  2) mixing a calcium carbonate suspension with the resulting mixture, mixing gluconic acid powders thereto to cure the mixture, and allowing carbon dioxide to foam, thereby obtaining composite biomaterials.

(10) The process according to (9), wherein the composite of hydroxyapatite and collagen has a microporous structure in which the c-axis of hydroxyapatite is oriented along the collagen fibers.

The present invention is hereafter described in detail.

1. Composite Biomaterials

1.1 Structure of Composite Biomaterials

The composite biomaterials of the present invention comprises hydroxyapatite, collagen, and alginate, and at least a part thereof is a microporous structure in which the c-axis of hydroxyapatite is oriented along the collagen fibers. This structure is specific to natural bones, which imparts mechanical properties specific to the composite biomaterials of the present invention.

The term "microporous structure" used herein refers to a structure similar to that of natural bones in which indefinite numbers of pores (gaps) of approximately several μm to several tens of μm are present.

The ratio of hydroxyapatite with collagen in the composite biomaterials of the present invention is generally between 60:40 and 90:10, and preferably between 70:30 and 85:15. This is because the ratio thereof needs to approximate the composition of natural bones (75:25).

The composite biomaterials of the present invention comprise alginates homogenously distributed therein. This makes the composite biomaterials more valuable for applications as implants and the like.

1.2 Constituents of Composite Biomaterials

The alginate content in the composite biomaterials of the present invention (after lyophilization) is 1 to 30% by mass, and preferably 5 to 20% by mass ("% by mass" is hereafter simply referred to as "%"), relative to the total amount of hydroxyapatite and collagen (total mass). Specifically, when the amount of alginate is too small, the strength of the composite becomes insufficient. In contrast, cell invasion into the biomaterials is blocked when the amount thereof is too large.

When the composite biomaterials of the present invention are used as bone fillers without curing and lyophilization, the composite biomaterials comprise an adequate amount of water, and their water contents can be adequately determined depending on applications.

When the composite biomaterials of the present invention are used after curing and lyophilization, a hydroxyapatite content of 55 to 80%, a collagen content of 10 to 35%, and an alginate content of 1 to 25%, relative to the entire composite biomaterials after lyophilization are preferable.

The composite biomaterials of the present invention have porosities (foamed portions) of 5 to 70%, and preferably approximately 10 to 50%, in a water-containing state before lyophilization. After the lyophilization, the composite biomaterials have porosities of at least 80%, and preferably at least 95%. As mentioned above, low porosity results in insufficient cell invasion into the biomaterials after implantation to the body, which in turn decreases bone inductivity and strength of the implants.

The lyophilized composite biomaterials of the present invention have gaps (pores) of between 1 μm and 500 μm (average diameter) and indefinite numbers of microgaps (micropores) of 1 μm or smaller. This microporous structure improves cell invasion and bone inductivity after implantation to the body.

2. A Process for Producing Composite Biomaterials

The process for producing composite biomaterials of the present invention comprises the following steps 1) and 2). Composite biomaterials having microporous structures in which alginates are homogenously distributed in composites of hydroxyapatite and collagen (hereafter referred to as "HAp/Col composite") can be obtained by this process:

1) mixing alginate in a HAp/Col composite; and
2) mixing a calcium carbonate suspension with the resulting mixture, mixing gluconic acid powders thereto to cure the mixture, and allowing carbon dioxide to foam, thereby obtaining composite biomaterials.

2.1 Step 1

(1) A HAp/Col Composite

A HAp/Col composite used in step 1) preferably has a microporous structure similar to that of natural bones in which the c-axis of hydroxyapatite is oriented along the collagen fibers. Such a composite can be produced in accordance with, for example, the method of Kikuchi et al. (Biomaterials 22, 2000, pp. 1705-1711). More specifically, a composite of interest can be obtained by simultaneously adding a calcium hydroxide solution and an aqueous phosphate solution containing collagen dropwise to a reaction vessel, and dehydrating the resulting sediment. Collagen used herein is not particularly limited. If the molecular weight of collagen is large, however, the strength of a composite becomes insufficient because of steric hindrance. Accordingly, the use of monomeric collagen is preferable. Pepsin-treated atelocollagen is particularly preferable for the composite biomaterials of the present invention because of its monomeric property and low antigenicity.

Preferably, a small amount of physiological saline, deionized water, a phosphate buffer, or the like is initially added to the above mentioned HAp/Col composite, and the resulting mixture is mixed by a homogenizer or other means. More specifically, when free calcium ion exists in the HAp/Col composite, it is sometimes reacted with alginic acid and cause gelatinization. Thus, calcium ion is allowed to adsorb on hydroxyapatite by adding physiological saline or the like, and it needs to avoid reaction with alginic acid.

When physiological saline or a phosphate buffer is added, ion penetrates the composite, and it is adsorbed on the surface of hydroxyapatite to neutralize its electric charge. This allows homogenous mixing of alginate and HAp/Col composite. Thus, the use of physiological saline or a phosphate buffer is particularly preferable. The amount of physiological saline, or the like, to be added varies depending on the structure and composition of the HAp/Col composite. It is preferably between 2 times and 6 times the total amount of the HAp/Col composite.

(2) Alginates

Alginates used in step 1) are not particularly limited, and sodium salt, potassium salt, and the like can be used. Crosslinked alginate may be used as alginates. Some of the crosslinked alginate has excellent bioabsorbability, and use thereof is more preferable. Alginates can be handled easily if they are prepared as 3-5% aqueous solutions.

2.2 Step 2

In step 2), gluconic acid and calcium carbonate are neutralized, carbon dioxide is then foamed, and alginic acid is cured by being crosslinked with calcium ion. Thus, composite biomaterials having microporous structures can be obtained.

(1) Neutralization (Foaming, Crosslinking)

Calcium carbonate used in step 2) is not particularly limited, and it may be a suspension or powder. Also, gluconic acid used in step 2) is not particularly limited.

The molar ratio of calcium carbonate to gluconic acid is between 1:3 and 2:3, and preferably about 1:2. The composite biomaterials of the present invention can have desired pore sizes and porosities through regulation of the amount of foaming by adequately adjusting the amounts of calcium carbonate and gluconic acid. When the amounts of calcium carbonate and gluconic acid are too small, gelatinization becomes insufficient. In contrast, an excess amount thereof results in excessive foaming. Too much or too little amount thereof decreases the strength of the composite biomaterials. Accordingly, calcium carbonate is preferably added in an amount of approximately 10% to 100% relative to the total amount of the HAp/Col composite. When only gluconic acid is added in an amount larger than the adequate level, the amount of foaming does not vary, while the crosslinking density is elevated by free calcium ions generated from the partially dissolved hydroxyapatite. Thus, the strength of the implant is enhanced.

When the composite biomaterials of the present invention are intended to be reinforced, the gelatinized mixture obtained in step 2) is immersed in a calcium hydrochloride solution or the like to crosslink alginic acid. Attention should be given to the density of crosslinking since cell invasion after implantation to the body will be adversely affected if crosslinking is too dense.

(2) Curing and Forming

The gelatinized mixture obtained in step 2) begins to cure within about several minutes to several tens of minutes, and the composite biomaterials of the present invention can be thus obtained.

The composite biomaterials can be used as bone fillers in that state if they are directly implanted to bone defects before curing.

When the production of an implants having a specific configuration and shape is intended, the composite biomaterials are injected into a desired mold immediately after the mixing in of gluconic acid, and then molded. When an enhanced level of curing is intended, lyophilization is carried out. The structures of the composite biomaterials, i.e., specific surface areas, porosities, pore (gap) sizes, and the like, can be suitably adjusted by selecting conditions for lyophilization (e.g., temperature, the duration of freezing, or lyophilization in water).

(3) Others

The composite biomaterials of the present invention may contain the essential components, i.e., hydroxyapatite, collagen, and alginate, as well as other components within the scope of the present invention. Examples of such components include Bone Morphogenetic Proteins, such as BMP2, BMP6, and BMP7, and growth factors, such as bFGF, aFGF, VEGF, and TGFβ.

3. Applications of Composite Biomaterials (1) Materials for Bone Regeneration (Implants)

As mentioned above, the composite biomaterials of the present invention can be used as bone fillers as they are if they are directly implanted to bone defects before curing. An implant having a desired configuration and shape can be produced by injecting the composite biomaterials into a desired mold immediately after the mixing in of gluconic acid.

The composite biomaterials of the present invention become as elastic as sponges and have excellent bioadaptability, bone inductivity, or bone conductivity upon moisture absorption. Specifically, when the biomaterials are implanted in bone tissues, they rapidly fused with the bone tissues, and integrated into the hard tissue of the recipient.

(2) Scaffold for Dell Culture

The composite biomaterials of the present invention can be used as a scaffold for cell and/or tissue culture. For example, bone marrow, liver, and other tissues can be reconstructed by conducting tissue culture using the composite biomaterials of the present invention containing highly bioactive cytokines as a scaffold under the biomimetic environment to which dynamics or electricity had been applied. Such scaffold enables effective reconstruction of damaged tissues when they are directly implanted in the body.

(3) Drug Carriers for Sustained Release

The composite biomaterials of the present invention can be used as sustained release agents for other bioactive substances, drugs, and the like. For example, when the composite materials of the present invention impregnated with anticancer agents are used for reconstructing bones resected due to osteogenic sarcoma, carcinoma recurrence can be prevented and the generation of hard tissue in the organism can be induced.

Accordingly, the composite materials of the present invention can be utilized as, for example, materials for bone regeneration capable of inducing and conducting bones, scaffold for bioactive agents or cell culture in tissue engineering containing amino acids, saccharides, and cytokines, and biocompatible drug carriers for sustained release. Specific examples of applications include artificial bones, artificial joints, cements for tendons and bones, dental implants, percutaneous terminals for catheters, drug carriers for sustained release, chambers for bone marrow induction, and chambers or scaffolds for tissue reconstruction.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

This description includes part or all of the contents as disclosed in the description of Japanese Patent Application No. 2001-328167, which is a priority document of the present application.

BEST MODES FOR CARRYING OUT THE INVENTION

The present invention is hereafter described in more detail with reference to the examples, although the technical scope of the present invention is not limited thereto.

EXAMPLE 1

Production of Composite Biomaterials of Hydroxyapatite/Collagen/Alginate

1. Method

At the outset, 3 ml of physiological saline was added to 500 mg of HAp/Col composite powders, the resultant was mixed by a homogenizer until a homogenous mixture was obtained. An aqueous solution of 3% sodium alginate (1.5 ml) was then added thereto, and the resultant was further mixed until it became homogenous. HAp/Col composite powders (500 mg) synthesized by the method of Kikuchi et al (Biomaterials 22, 2000, pp. 1705-1711) were used as composites of hydroxyapatite and collagen (HAp/Col composites).

Subsequently, 80 μl of a 5M calcium carbonate suspension was added thereto, the resultant was mixed, and 100 mg of gluconic acid powder was then added thereto, followed by mixing.

The resulting mixture was immediately placed in the mold and then allowed to cure over the period of 45 minutes. This cured product was allowed to freeze at −20° C. for 12 hours and then lyophilized. Thus, the composite biomaterials (implants) of the present invention were obtained.

2. Results (Properties of Composite Biomaterials)

Figure 1:
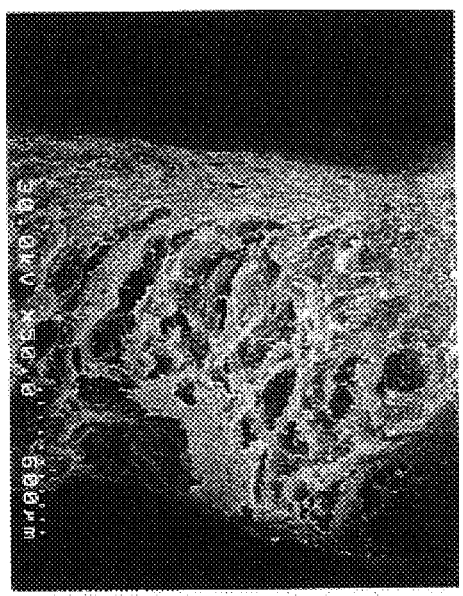
FIG. 1 is a scanning microscope photograph of the implant prepared in Example 1.
Figure 1:
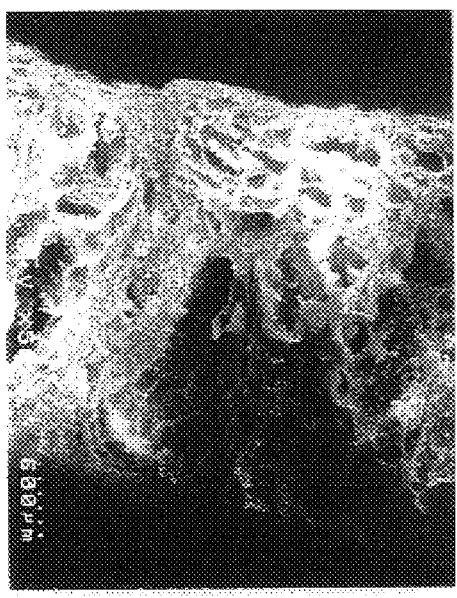
Figure 1:
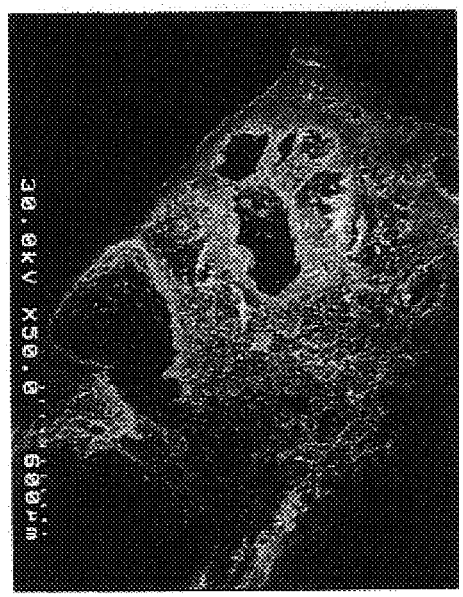
Figure 1:
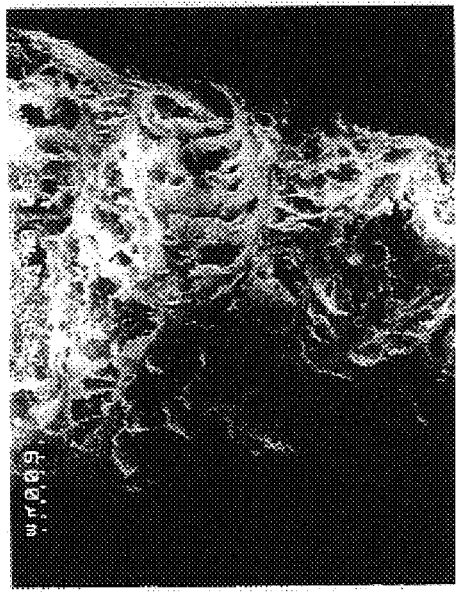

Profile sections of the implants were observed using a scanning microscope. The implants were found to be porous bodies having pores of several μm to several hundreds of μm (diameter) and had microporous structures similar to those of natural bones (FIG. 1).

EXAMPLE 2

Experiment of Implantation into Rat Femurs

1. Method

A hole was provided in the distal part of a 10-week-old Wistar rat femur, and the implants prepared in Example 1 (2×2×5 mm) were implanted thereinto. The implants were taken out 2, 4, 6, and 8 weeks after the implantation and subjected to HE staining and toluidine blue staining. As controls, the following three kinds of substances were implanted to the distal part of the rat femurs and evaluated in the same manner as mentioned above. FIGS. 2 to 5 show the results of HE staining 2, 4, and 8 weeks after implantation of each sample.

(i) Commercialized sintered porous hydroxyapatite (2×2×5 mm, BONFIL, Mitsubishi Materials Corporation).

(ii) A compressed form of HAp/Col composite used in Example 1 (2×2×5 mm).

(iii) A solution of 3% sodium alginate powders (sodium alginate (500-600 cP), Wako Pure Chemical Industries, Ltd.) (physiological saline).

2. Results

1) The Implants of the Present Invention

Figure 2:
FIG. 2 is a photograph showing an image of HE-stained tissues 2, 4, and 8 weeks after the implantation of the implant of the present invention in Example 2.
Figure 2:
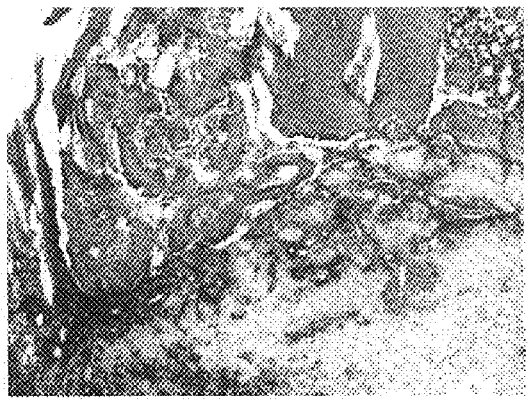
Figure 2:
Figure 2:
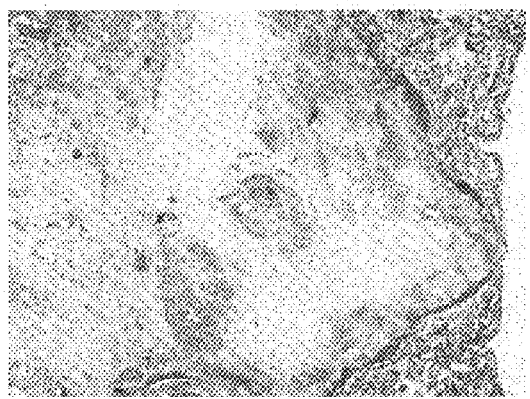
Figure 2:
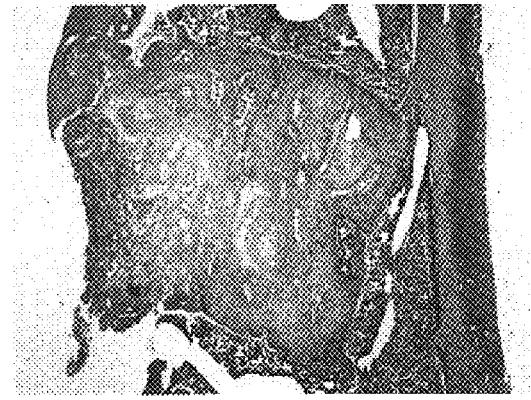
Figure 2:
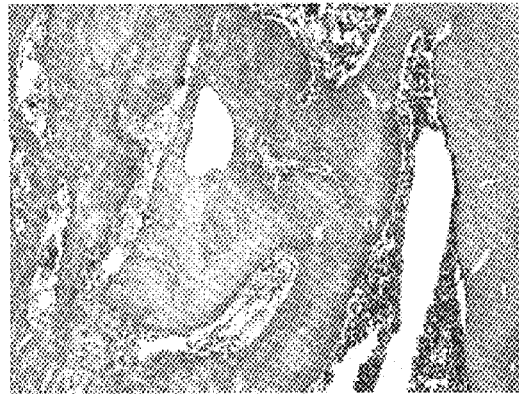

As is apparent from FIG. 2, bones in contact with the implants were already actively formed in the vicinity of the implants of the present invention by the second week. After 4 weeks or 8 weeks, cell invasion also increased. As is apparent from an enlarged view, in addition to the enhanced cell invasion after 4 weeks or 8 weeks, osteogenesis was also enhanced inside the implants. Thus, cell invasion into the implants was relatively good, and multinucleated giant cells considered to be "phagocytes" also invaded into the implants. Osteogenesis occurred at the sites where bones were in direct contact with the implants, and thus, the boundaries between the implants and new bones were unclear. No inflammatory reaction was observed as a result of toluidine blue staining.

2) Commercialized Sintered Porous Hydroxyapatite

Figure 3:
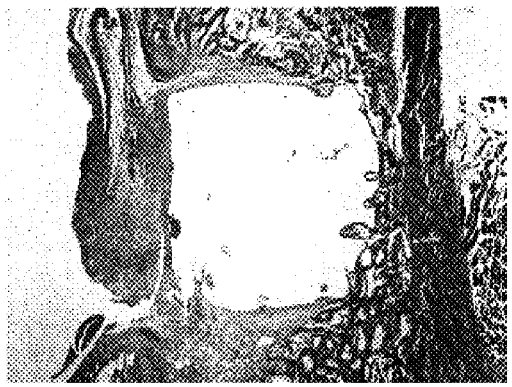
FIG. 3 is a photograph showing an image of HE-stained tissues 2, 4, and 8 weeks after the implantation of commercialized porous HAp in Example 2.
Figure 3:
Figure 3:
Figure 3:
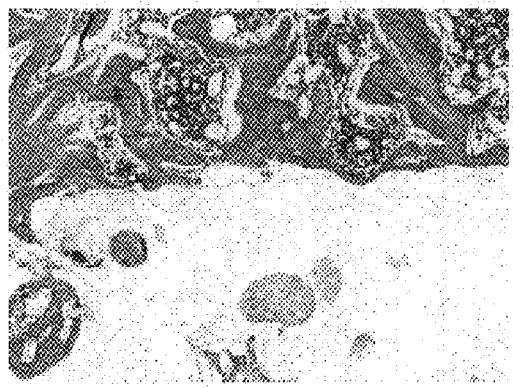
Figure 3:
Figure 3:
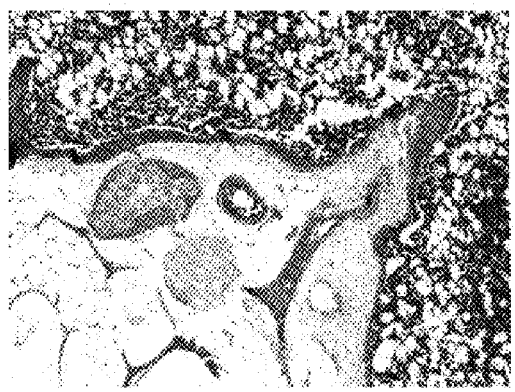

As is apparent from FIG. 3, bones in contact with the hydroxyapatite were already actively formed in the vicinity of the commercialized hydroxyapatite by the second week. However, cell invasion into the hydroxyapatite did not increased very much even after 4 weeks or 8 weeks. As is apparent from an enlarged view, osteogenesis was also enhanced inside the hydroxyapatite after 4 weeks or 8 weeks. Also, in spite of its porous structure, cell invasion was not found in most of the pores. Intensive inflammatory reaction was not observed.

3) A Compressed form of HAp/Col Composite

Figure 4:
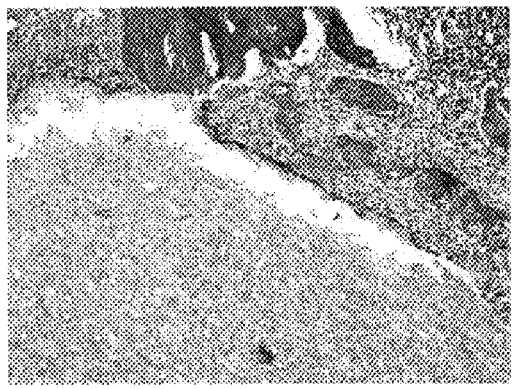
FIG. 4 is a photograph showing an image of HE-stained tissues 2, 4, and 8 weeks after the implantation of a HAp/Col composite in Example 2.
Figure 4:
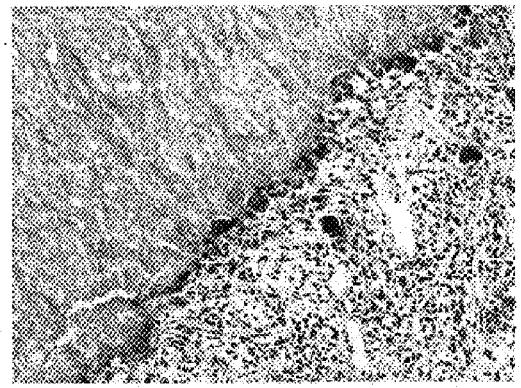
Figure 4:
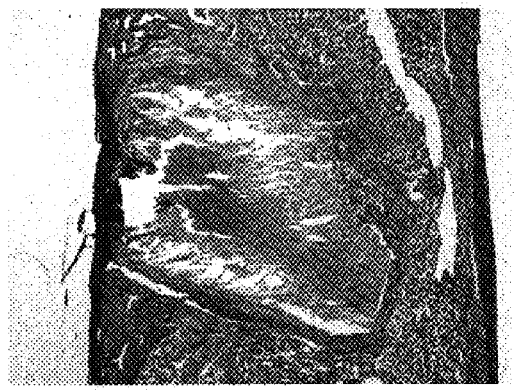
Figure 4:
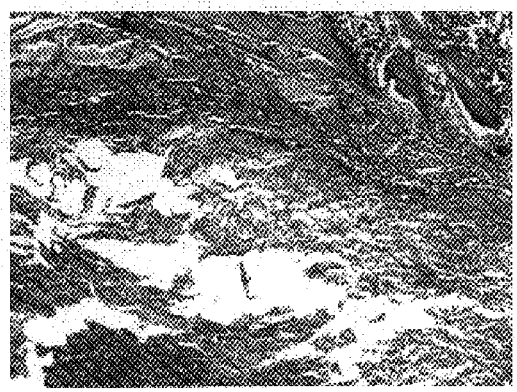
Figure 4:
Figure 4:
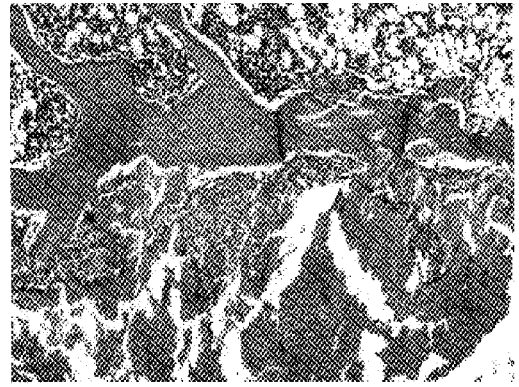

As is apparent from FIG. 4, cell invasion into the HAp/Col composite was not found by the second week. Although resorption of the HAp/Col composite made progress after 4 weeks or 8 weeks, cell invasion did not yet increased into the HAp/Col composite that were not resorbed. As is apparent from the enlarged view, resorption of HAp/Col composite made progress with time, and cell invasion was found at the site of the resorption. Osteogenesis took place outside of the fibrous tissue in such a manner that osteogenesis followed the implant resorption.

4) A Solution of 3% Sodium Alginate

Figure 5:
FIG. 5 is a photograph showing an image of HE-stained tissues 2, 4, and 8 weeks after the implantation of sodium alginate in Example 2.
Figure 5:
Figure 5:
Figure 5:
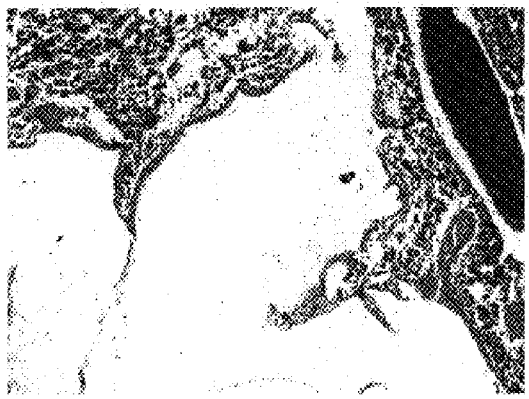
Figure 5:
Figure 5:

As is apparent from FIG. 5, bones partially in contact with the sodium alginate were formed. However, the degree of cell invasion was low even after 8 weeks. Intensive inflammatory reaction was not observed. An enlarged view also represents the similar results.

3. Conclusions

Accordingly, the implants (composite biomaterials) of the present invention were found to have bioadaptability, the capacity for cell invasion, and the capacity for osteogenesis better than other porous substances. The composite biomaterials of the present invention were found to be excellent in terms of safety since no inflammatory reaction was observed after implantation.

All publications, patents, and patent applications cited herein are incorporated herein by reference in their entirety.

INDUSTRIAL APPLICABILITY

The present invention provides novel composite biomaterials having excellent bioadaptability and bone inductivity.

The invention claimed is:

1. A composite biomaterial, comprising hydroxyapatite, collagen fibers, and alginate, wherein the composite biomaterial contains homogenously crosslinked alginate contained in a microporous structure of hydroxyapatite and collagen fibers, wherein the c-axis of the hydroxyapatite is oriented along the collagen fibers, and wherein the composite biomaterial is produced by the steps of:

a) mixing a composite of hydroxyapatite and collagen having a microporous structure in which the c-axis of the hydroxyapatite is oriented along collagen fibers with alginate;

b) mixing a calcium carbonate suspension with the composition produced in step a); and c) mixing gluconic acid powder with the composition produced in step b) to cure the composition by crosslinking the alginate, and allowing carbon dioxide to foam, thereby obtaining the composite biomaterial.

2. The composite biomaterial according to claim 1, wherein the alginate content is 1 to 30% by mass, relative to the total amount of hydroxyapatite and collagen fibers.

3. The composite biomaterial according to claim 2, wherein the alginate content is 5 to 20% by mass, relative to the total amount of hydroxyapatite and collagen fibers.

4. The composite biomaterial according to claim 3, wherein the ratio of hydroxyapatite to collagen fibers is between 60:40 and 90:10.

5. The composite biomaterial according to claim 4, wherein the ratio of hydroxyapatite to collagen fibers is between 70:30 and 85:15.

6. A process for producing a composite biomaterial, comprising hydroxyapatite, collagen fibers, and alginate, wherein the composite biomaterial contains homogenously crosslinked alginate contained in a microporous structure of hydroxyapatite and collagen, wherein the c-axis of the hydroxyapatite is oriented along the collagen fibers, the process comprising the following steps:

1) mixing a composite of hydroxyapatite and collagen fibers, the composite having a microporous structure in which the c-axis of the hydroxyapatite is oriented along the collagen fibers, with alginate; and 2) mixing a calcium carbonate suspension with the composition produced in step 1); and 3) mixing gluconic acid powder with the composition produced in step 2 to cure the mixture by crosslinking the alginate, and allowing carbon dioxide to foam, thereby obtaining the composite biomaterial.

7. The composite biomaterial of claim 1, which is lyophilized after it is obtained in claim 1, step c).

8. The composite biomaterial according to claim 7, wherein the composite biomaterial after lyophilization has a porosity of 80% or higher.

9. The process according to claim 6, wherein the alginate content in the composite biomaterial is 1 to 30% by mass, relative to the total amount of hydroxyapatite and collagen fibers.

10. The process according to claim 6, wherein the alginate content in the composite biomaterial is 5 to 20% by mass, relative to the total amount of hydroxyapatite and collagen fibers.

11. The process according to claim 10, wherein the ratio of hydroxyapatite to collagen in the composite biomaterial is between 60:40 and 90:10.

12. The process according to claim 11, wherein the ratio of hydroxyapatite to collagen fibers in the composite biomaterial is between 70:30 and 85:15.

13. The process according to claim 6, further comprising the step of lyophilization of the composition obtained in step 3).

14. The process according to claim 13, wherein the composite biomaterial after lyophilization has a porosity of 80% or higher.

* * * * *